(12) United States Patent
von der Ruhr et al.

(10) Patent No.: US 6,308,089 B1
(45) Date of Patent: Oct. 23, 2001

(54) LIMITED USE MEDICAL PROBE

(75) Inventors: Gerhard von der Ruhr, Brookfield; Dennis E. Bahr, Madison; Michael T. Larsen, Brookfield, all of WI (US)

(73) Assignee: O.B. Scientific, Inc., Brookfield, WI (US)

( * ) Notice: Subject to any disclaimer, the term of this patent is extended or adjusted under 35 U.S.C. 154(b) by 0 days.

(21) Appl. No.: 09/291,769

(22) Filed: Apr. 14, 1999

(51) Int. Cl.[7] .................................................. A61B 5/04
(52) U.S. Cl. .............................................. 600/338; 600/588
(58) Field of Search ........................... 600/588, 639, 600/325, 338, 372–377

(56) References Cited

U.S. PATENT DOCUMENTS

| | | | | |
|---|---|---|---|---|
| 4,898,179 | * | 2/1990 | Sirota ................................. | 600/486 |
| 5,155,697 | * | 10/1992 | Altmayer et al. .................... | 364/550 |
| 5,162,725 | * | 11/1992 | Hodson et al. ...................... | 324/115 |
| 5,228,440 | * | 7/1993 | Chung et al. ........................ | 600/338 |
| 5,400,267 | * | 3/1995 | Dinen et al. ......................... | 364/552 |
| 5,411,024 | * | 5/1995 | Thomas et al. ...................... | 600/325 |
| 5,438,996 | * | 8/1995 | Kemper .............................. | 600/437 |
| 5,645,563 | * | 7/1997 | Hann et al. .......................... | 606/202 |

FOREIGN PATENT DOCUMENTS

WO 00/53082    9/2000   (WO).

* cited by examiner

Primary Examiner—Cary O'Connor
Assistant Examiner—Pamela Wingood
(74) Attorney, Agent, or Firm—Reinhart, Boerner, Van Deuren, Norris & Rieselbach, s.c.

(57) ABSTRACT

A limited use medical probe is disclosed. The medical probe includes a memory storage component for maintaining a use value, representing either the number of uses and/or the duration of use of the medical probe. The medical probe is coupled to a medical monitoring device which prevents the performance of monitoring functions when the number of uses or the total duration of use reaches a predetermined threshold value, thereby preventing overuse of the probe.

34 Claims, 5 Drawing Sheets

LIMITED USE MEDICAL PROBE

FIELD OF THE INVENTION

The present invention relates generally to medical sensor devices and methods for measuring clinical physiological parameters including vital signs. More particularly, the invention is concerned with a medical monitoring system that limits the duration and/or number of uses of an associated sensor device to prevent overuse and potential failure.

BACKGROUND

Medical sensor devices, such as internal probes that are inserted into a body cavity or under the skin of a patient in order to monitor biological parameters, are well known in the art. Typically, such devices comprise a housing including at least one monitoring element such as a pressure sensor, a light emitting device and associated detector, an ECG sensor, or other vital sign monitoring device. One particular example of a medical sensor device is fetal sensor, such as that described in U.S. Pat. No. 5,425,362. Fetal sensors are inserted into the uterine wall of a mother to noninvasively monitor the condition of a fetus, a mother, and a placenta.

One problem associated with known medical sensor devices is that they have a limited life span. Sensor devices are prone to wear through repeated use or through extended use over a period of time. Problems associated with such overuse include spurious readings as internal wires and connectors become loose. More importantly, sensor devices that are used repeatedly or over an extended period of time are prone to break. Once such an incident occurs, it is often difficult to determine when the sensor failed, or to track the cause of such an occurrence.

To prevent these problems, medical clinicians may limit the number and duration of uses of a given medical sensing device through an equipment log or other manual system. While such systems may be effective in certain circumstances, they rely heavily on manual records, which are time-consuming and difficult to maintain, particularly since the cooperation of a number of clinical personnel is required. In busy hospital settings, and especially in emergency situations, such systems are difficult to manage and are easily overlooked or ignored.

There remains, therefore, a need for a medical monitoring system that can automatically limit the usage of medical sensor devices. Such a system would preferably limit the duration or number of uses of a given medical sensing device to a predetermined limit value. Preferably, the medical monitoring system would also provides additional functions, such as error checking, time and date stamping, and security checking.

It is therefore an object of the invention to provide a medical monitoring system that can limit the number of times a medical sensor device is used.

It is another object of the invention to provide a medical monitoring system that can limit the duration of the use of a medical sensor device.

It is still another object of the invention to provide a medical monitoring system that provides a time and date stamp to identify monitoring processes performed by monitoring equipment.

It is a still further object of the invention to provide a medical sensor device that can store information regarding the duration of use of the device.

It is another object of the invention to provide a medical monitoring device that can store information regarding the number of times the device has been used.

It is a yet further object of the invention to provide a medical monitoring system that can provide product identity of an associated medical sensor device.

It is still another object of the invention to provide a medical monitoring system that includes a security function for verifying the identity of attached sensors.

It is yet another object of the invention to provide a medical monitoring system that includes a security function to prevent tampering with stored data.

SUMMARY OF THE INVENTION

In one aspect, the present invention is a medical probe that includes at least one sensor device and a memory storage component capable of communicating with external devices for maintaining data about usage of the probe. The memory storage component can include information regarding the number of times the medical probe has been used, the duration of each use, the total duration of use, and other information regarding the duty cycle of usage of the medical probe. Other parameters, including the date and time of a given use of the sensor, the date and time when a given condition occurred, product identity, clinical information such as patient or doctor data, and other medical information can also be stored in the memory storage location of the sensor device. The medical probe is preferably identified by a unique serial number that can be used in a security function to identify the device and prevent tampering with the use data.

The medical probe is coupled to a monitoring device to provide a medical monitoring system. The monitoring device, through communications with the medical probe, determines usage of the medical probe and limits the total use of each medical probe to a limit value by preventing use beyond a predetermined limit. The limit, as noted above, can be based on either total number of uses, total duration of use, or a combination of both. The monitoring device, in conjunction with the medical probe, provides a security function for verifying the identity of the sensor device. Preferably, the security function operates on internal serial numbers and encryption keys to ensure that the proper probes are coupled to the monitoring system, that the internal use data has not been tampered with, and to verify communications between the medical probe and monitoring device.

The monitoring system can also provide a series of product identity functions, as well as stored data for identifying the equipment used in a given monitoring procedure. The stored data can include serial numbers of the equipment used, a date and time stamp, information regarding the medical personnel involved in a monitoring procedure, patient data, and other information.

In one highly preferred embodiment of the invention, the medical monitoring system comprises a fetal sensor for monitoring oxygen saturation in the blood of a fetus while in the womb. Preferably the memory storage component comprises a token counter chip that is coupled directly to the fetal sensor connector. The token counter chip preferably includes memory storage, a counter that can store a use value, and a built-in security function to prevent tampering.

Other advantages and features of the invention, together with the organization and manner of operation thereof, will become apparent from the following detailed description when taken in conjunction with the accompanying drawings wherein like elements have like numerals throughout the drawings.

DETAILED DESCRIPTION OF THE PREFERRED EMBODIMENTS

Figure 1:
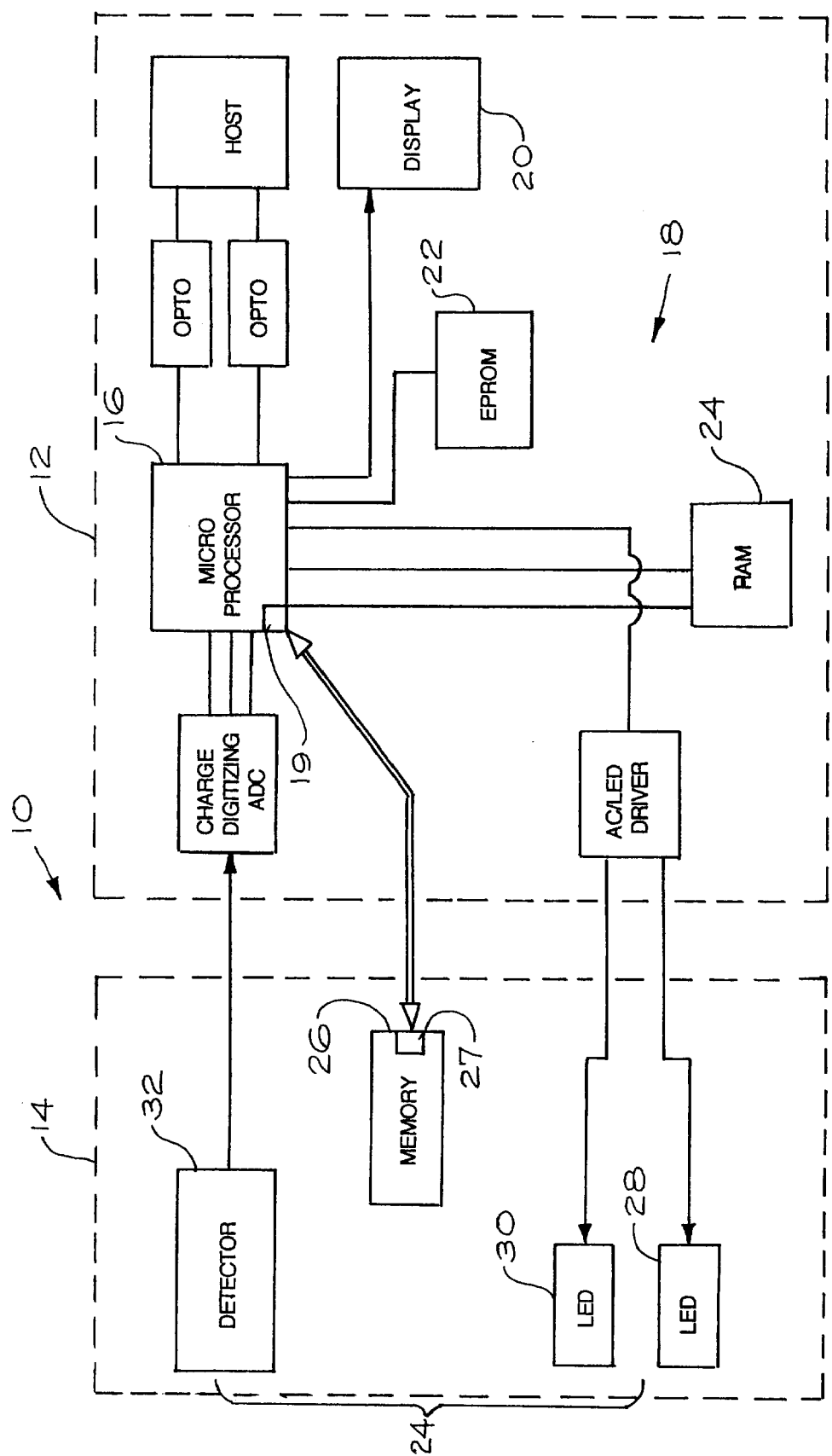
FIG. 1 is a block diagram of a medical monitoring system constructed in accordance with one embodiment of the present invention.

Referring now to the figures, and more particularly to FIG. 1, a block diagram of a medical monitoring system constructed in accordance with one preferred embodiment of the present invention is shown at 10. Generally, the medical monitoring system 10 comprises a monitoring device 12 and a medical probe 14.

Preferably, the monitoring device 12 includes a controller 16, at least one memory storage component 18, and a display 20. Preferably, the controller 16 includes a communications port 19 for communicating with external devices, either serially or through other types of digital communications. In some applications, however, additional types of communication devices may also be used. The controller 16 is preferably a microprocessor, but can comprise a microcontroller or various other types of control devices. Furthermore, although the memory component 18 is shown as comprising a RAM device 22 and an EPROM 24, other known types of memory devices may be used without departing from the invention. Preferably, the monitoring device will include nonerasable memory components for storing a serial number, as will be described more fully below. In some applications, the controller 16 may include an on board memory component 18, thereby eliminating the need for external memory devices.

The medical probe 14 generally comprises a sensor 24 and a memory storage component 26. The sensor 24 may comprise any of a number of sensor devices including pressure sensors, ECG sensors, EEG sensors, temperature sensors, oxygen sensors, ultrasound transducers, chemical sensors, or, as shown, light emitting devices 28, 30 and associated detector 32. The selection of sensor devices 24 and associated hardware used in the medical monitoring system 12 is dependent only on the type of medical monitoring to be performed without reference to other aspects of the invention. The memory storage component 26 can comprise a number of various known devices including microcontrollers or microprocessors, EPROMS, EEPROMS, or application specific chips. These devices provide a memory location for maintaining data concerning use of the medical probe 14. The memory storage component 26 also includes communication capabilities such as a serial communications port 27 or other digital communication means. In some applications, separate communication devices may also be included. Preferably, more sophisticated devices that provide functions such as product identity, security checking, and date and time stamping are used. In one highly preferred embodiment of the invention, the memory storage component comprises a token card chip that includes both memory storage and security functions. Other highly preferred devices include EEPROMS with built-in CRC and serial number functions. These preferred devices will be described more fully below.

As noted above, an important function of the memory storage component 26 is to provide a storage location for maintaining data regarding the duration of use of the medical probe 14, and/or to maintain a history of the number of uses of the medical probe 14. This data will hereinafter be referred to as the use value. The memory storage component can also store security information such as serial numbers, product identity and encryption keys; troubleshooting data such as date and time stamp data, the identity of medical workers involved in the monitoring process, and patient data; and other types of data. In alternative embodiments, the memory storage component 26 may also be used to store the results of error checking routines and other testing data. The memory storage 18 of the monitoring device 12 preferably also includes security information including serial numbers identifying the monitoring device and encryption keys, that can be used to verify communications and identify devices as will be described below. For security reasons, this information is preferably stored in nonerasable memory components (not shown). The memory storage 18 preferably also stores troubleshooting and calibration information to provide a cross check against the information stored in the medical probe 14.

In initial setup stages, an initial use value representing either a count or time duration is written into the memory storage component 26. A serial number identifying the medical probe 14, and one or more encryption keys can also be stored in the memory storage component 26. The serial number is preferably used to identify a specific medical probe 14, as well as to identify a type of probe. Serial number and encryption keys are also preferably stored in the memory component 18 of the monitoring device 12. As noted above, this type of information is preferably stored in nonerasable memory locations. The serial numbers and encryption keys can be used to provide a security function, as described below.

Figure 2:
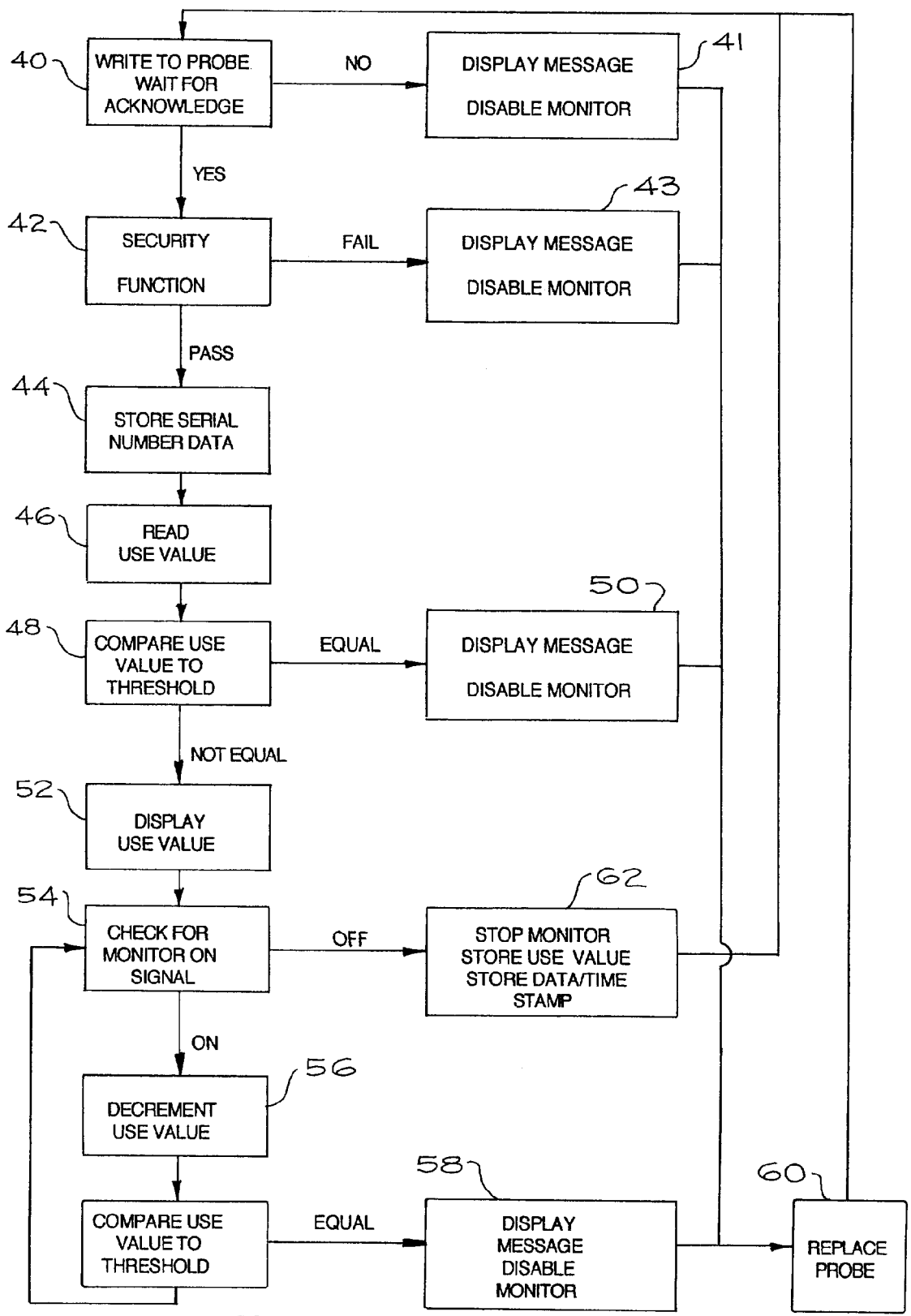
FIG. 2 is an operational block diagram of a medical monitoring system constructed in accordance with one embodiment of the present invention.

Referring now to FIG. 2, an operational block diagram of one embodiment of the medical monitoring system 10 is shown. To ensure a proper connection and verify that a proper medical probe 14 is coupled to the monitoring device 12, an initial query can be transmitted to the medical probe 14. After transmitting such a query to the medical probe 14, the medical monitoring device 12 waits for an acknowledge signal from the medical probe 14 prior to performing any further steps. The query and acknowledge sequence 40 verifies that the memory storage component 26 is receiving power and can communicate with the controller 16 in the monitoring device 12 through a serial or other communications link. If no acknowledgment is received, the controller 16 of the medical device 12 will determine that the medical probe 14 currently attached is an incorrect device or is not functional. Preferably, the controller will provide a message to the display 20 and disable monitoring functions until a suitable medical probe 14 is attached (Step 41). Although a query and acknowledge step is shown, it will be apparent to one of ordinary skill in the way that the step is not required. Furthermore, the ability to perform this step will depend on the functionality of the component chosen as the memory storage component 26 in the medical probe 14.

To further ensure that a proper medical probe 14 is coupled to the monitoring devices 12, to secure communications between the devices, and to prevent tampering with the use value stored in the memory storage component 26, the medical monitoring system 10 of the present invention preferably uses the serial numbers and encryption keys described above to provide a security function 42. Each serial number is preferably encrypted and serially transmitted to the other device (i.e. from the medical probe 14 to the monitoring device 12 and from the monitoring device 12 to the medical probe 14), which includes the numerical encryption keys and algorithms to decrypt the transmitted data. Encryption can be provided through known systems such as cyclical redundancy checks and/or public key encryption systems that serve not only to verify transmissions, and validate data, but also to determine a signature of the transmitted data, thereby identifying the specific sending device. Preferably, the monitoring device 12 cannot access the use value stored in the memory storage component 26 until the identity of the monitoring device 12 is established. If the security function fails to verify the identify of the probe 14, a message is preferably written to the display 20 of the monitoring device 12 and the controller 16 of the monitoring device 12 disables monitoring functions until a new medical probe 14 is attached (Step 43). Preferably, the security function also verifies the contents of the memory component 26 has not been tampered with before proceeding.

Upon completion of the security check, the identity of the medical probe 14, as defined by the serial number, is preferably stored in the memory 18 of the monitoring system 12 for identification purposes. The serial number of the monitoring device 12 can also be stored in the memory storage component 26 to provide a cross check, as will be described more fully below (Step 44). The monitoring system 12 can also use the serial number and other identification information to determine the type of probe being used. For example, the monitoring system 12 can determine if the attached medical probe 14 is a fetal monitoring sensor, a finger sensor, or other sensor device more commonly used with adults. Using this information, the monitoring system 12 can adjust monitoring parameters and algorithms to meet specific monitoring requirements.

Once the identity and contents of the memory storage component 26 of the memory probe 14 are verified, the monitoring device 12 reads the use value (Step 46) from the memory storage component 26 and preferably stores the value in internal memory 18 of the monitoring device 12. The use value can then be compared to a stored threshold value representing the probe use limit in terms of either count or duration to verify that the use value associated with the medical probe 14 has not reached the limit. (Step 48) If the use value is substantially equivalent to the threshold value, a message indicating that a new probe is required is preferably written to the display 20, and monitoring functions are disabled until a suitable probe is connected to the monitoring device 12. (Step 50). In some embodiments the use value is written to the display 20 by the controller 16 to alert medical personnel to the remaining usefulness of the medical probe 14 (Step 52). If the amount of time or number or remaining uses is limited, this information can be used to determine whether to replace the medical probe 14 or proceed with the procedure. In alternative embodiments, an error checking routing, wherein each of the sensors 24 of the medical probe 14 are activated to verify proper output can be performed prior to using the probe 14. The results of these tests can be stored in internal memory of the memory storage device 26 in the medical probe 14, written to the memory 18 of the monitoring device 12, written to the display 20 for immediate review by medical personnel, or a combination of the above. In some applications, where the memory storage component 26 is a microcontroller, microprocessor, or other device with more advanced mathematical capabilities, the use value can be maintained in the memory storage component 26 and updated internally.

Any signal normally used by the monitoring device 12 to begin a monitoring sequence can be used as a signal to commence changing the use value (Steps 54 and 56). Examples of suitable signals are reading an activated pushbutton or other switching device, reading an input signal from an external device, or, in some applications, connecting the medical probe 14 to the monitoring device 12. In applications where the use value is a count representing a number of total uses, the use value must be changed only once for each monitoring sequence. In these types of applications, when the use value reaches a predetermined number of uses, a message is preferably written to the display 20 of the monitoring device 12. Preferably, a warning will be written to the display 20 by the controller 16 prior to the last use, thereby allowing medical personnel to obtain a new probe for replacement. In some applications, a continual count may be maintained on the display 20 of the monitoring device 12. Once the use value has reached the threshold use value, the controller 16 in the monitoring device 12 will prevent any additional monitoring sequences (Step 58) until the medical probe 14 is replaced (Step 60). Although changing the use value from an initial use number has been described, it will be apparent to one of ordinary skill in the art that the system 10 could be easily modified to increment, decrement, or use an apparent random sequence.

In applications where the monitored value is a duration of time, a timing function must be activated when a monitoring sequence begins. Preferably, the timing function is performed by the controller 16 in the monitoring device 12, but in applications where the memory storage device 26 is a microcontroller or other device capable of providing a timing function, the timing function may be performed in the medical probe 14. When the duration of use of the medical probe 14 is substantially equivalent to a predetermined value, a signal is preferably sent to the display 20 of the monitoring device 12 warning that the limit has been reached. The signal can comprise a message written to an alphanumeric display. Alternatively, the display 20 may comprise a bank of indicator lights or LEDs that provide use and error information. Upon reaching the use limit, the medical probe 14 will preferably continue to operate until the monitoring sequence is complete. Prior to beginning another monitoring sequence, however, the monitoring device 12 will read the use value and will not allow another monitoring sequence to begin until the medical probe 14 is replaced. Again, the timing function can be operated to count either up to a known value, or down from an initial value to zero.

When the monitoring signal is dropped, or a stop monitoring signal is received, (Step 62) a date and time stamp, along with the identification information of the medical probe 14, is preferably stored in the memory 18 of the monitoring device, and can be used in conjunction with clinical logs to track the identity of the equipment and the personnel that were involved in a given monitoring procedure. In some applications, the monitoring device 12 may include input devices such as keyboards, serial links, and other communication devices, for logging the identity of clinicians and the patient involved in a procedure, thereby providing a complete log for later review. In a preferred embodiment, RFS identification functions can be incorporated in the monitoring device 12 to identify medical personnel, patients, and other information. Preferably, date and time stamps, identification of the monitoring device 12, and other identifying information is stored in both the memory storage component 26 of the medical probe 14 and the memory 18 of the monitoring device 12 as a cross check. Storing this information in both locations simplifies the process of later identifying the equipment used in a given monitoring process in the event of a failure. In some applications, detailed information regarding medical parameters encountered in a given procedure may be stored. Alternatively, the controller may check for defined errors or conditions and store data when such conditions occur. Although storing date and time stamp information at the end of a monitoring sequence has been described, it will be apparent to one of ordinary skill in the art that this step could also be taken at the beginning of a monitoring sequence, after the occurrence of predefined conditions, in the event of a serial failure, periodically, or in a number of other ways.

Although a distinct functional block diagram has been shown, it will be apparent to one of ordinary skill in the art that changes in the order of certain functions, modifications of functions, and additions could be made without departing from the invention.

Figure 3:
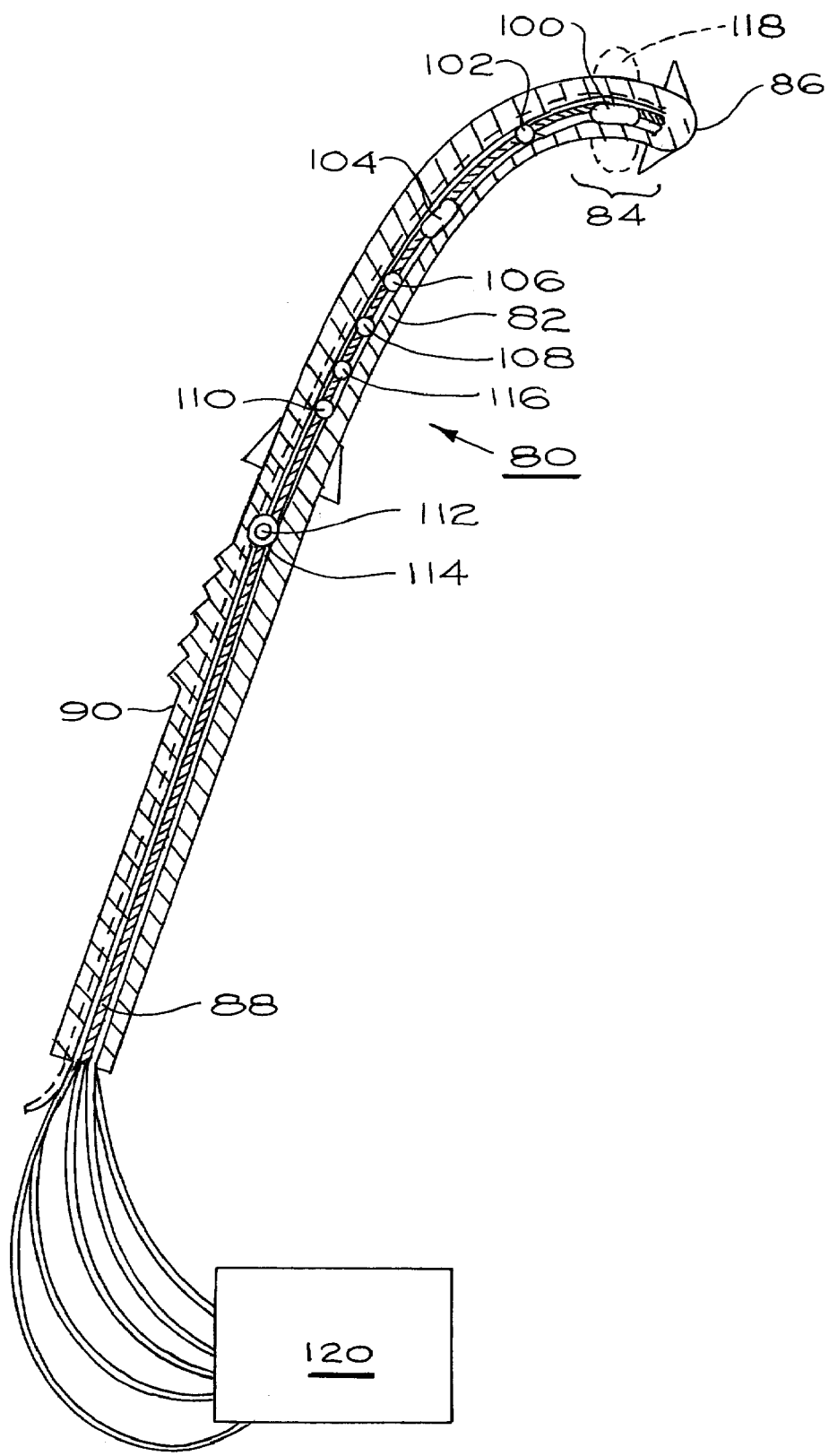
FIG. 3 is a fetal sensor monitor constructed in accordance with one embodiment of the present invention.

The problems associated with prior art medical sensing devices are particularly acute in fetal monitoring devices. Consequently, in a highly preferred embodiment of the present invention, the medical probe 14 comprises a fetal sensor device 80, as can be seen in FIG. 3. This device is more fully described in U.S. Pat. No. 5,425,362 which is incorporated herein by reference. The fetal sensor device 80 (hereinafter "device 80") includes a housing 82 and a flexible distal end portion 84 with a soft molded tip 86. Preferably the distal end portion 84 is integrally coupled to the remainder of the device 80. The flexible distal end portion 84 and the soft molded tip 86 help minimize the possibility of membrane rupture. As shown in FIG. 3, the device 80 includes a flexible strip 88 (such as spring steed coated with a smooth surfaced coveting 90)(such as a silicone rubber or Teflon).

The device 80 can include preferably one or more of a variety of sensors, such as a pressure sensor 100, an ECG sensor 102, an EEG sensor 104, a temperature sensor 106, an oxygen sensor 108, an ultrasound transducer/sensor 110, a laser diode 112 emitting IR signals with an associated sensor 114, and a chemical sensor 116. In some applications, the pressure sensor 100 can include a balloon type device 118 that can be inflated to variable pressures and used with conventional feed back electronics to maintain a substantially constant pressure of engagement of the device 100 with at least one of the fetus and the uterus of the mother.

Figure 4:
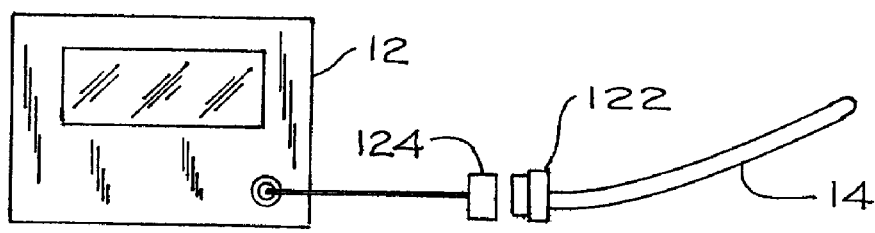
FIG. 4 is a simplified view of a medical monitoring system constructed in accordance with the present invention.
Figure 5:
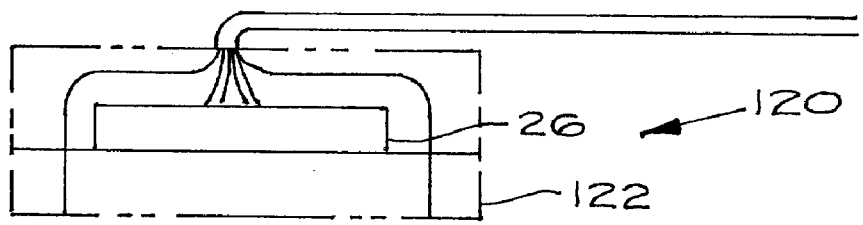
FIG. 5 is a simplified internal view of the connector shown in FIG. 4.

In a preferred embodiment, the device 80 uses the various sensors described hereinbefore to measure fetal heart rate (the ECG sensor 102), oxygen saturation in the fetal blood (the oxygen sensor 108 which generally comprises one or more light emitting diodes and associated detectors (not shown), and differences in fetal versus uterine temperature (the temperature sensor 130) to allow a three-pronged decision tree analysis to assess fetal wellness. If there is uterine-placental-fetal insufficiency, there is usually a rapid rise in fetal temperature since fetal heat loss is facilitated by heat exchange by the well-perfused placenta 136. Performance of oximetry studies can differentiate between clinically insignificant marginal heart rate values and significant fetal distress. It is also useful to accumulate ECG data to ascertain the need to deliver a child when a condition of fetal distress occurs. Although a fetal sensor 80 for monitoring a number of medical parameters has been shown, it will be apparent to one of ordinary skill in the art that any combination of sensors could be used depending on the desired application. In preferred embodiments, the device 80 can comprise an oximetry sensor including two or more light emitting devices of varying wavelengths and corresponding detectors. Reflection and absorption of the light is used to calculate oxygenation levels in known ways. In this application the monitoring device 12 comprises an oximeter for calculating the oxygenation levels Referring again to FIG. 3, all of the sensor connections are routed to a single electrical connection point designated 120. In a preferred embodiment, the connection point 120 comprises a connector 122 (FIGS. 4 and 5) that couples to a mating connector 124 to the monitoring device 12. The memory storage component 26 is preferably coupled directly to the connector 122 to limit the overall size of the medical probe. Power for the fetal sensor 80 is provided, preferably, by the monitoring device 12.

Figure 6:
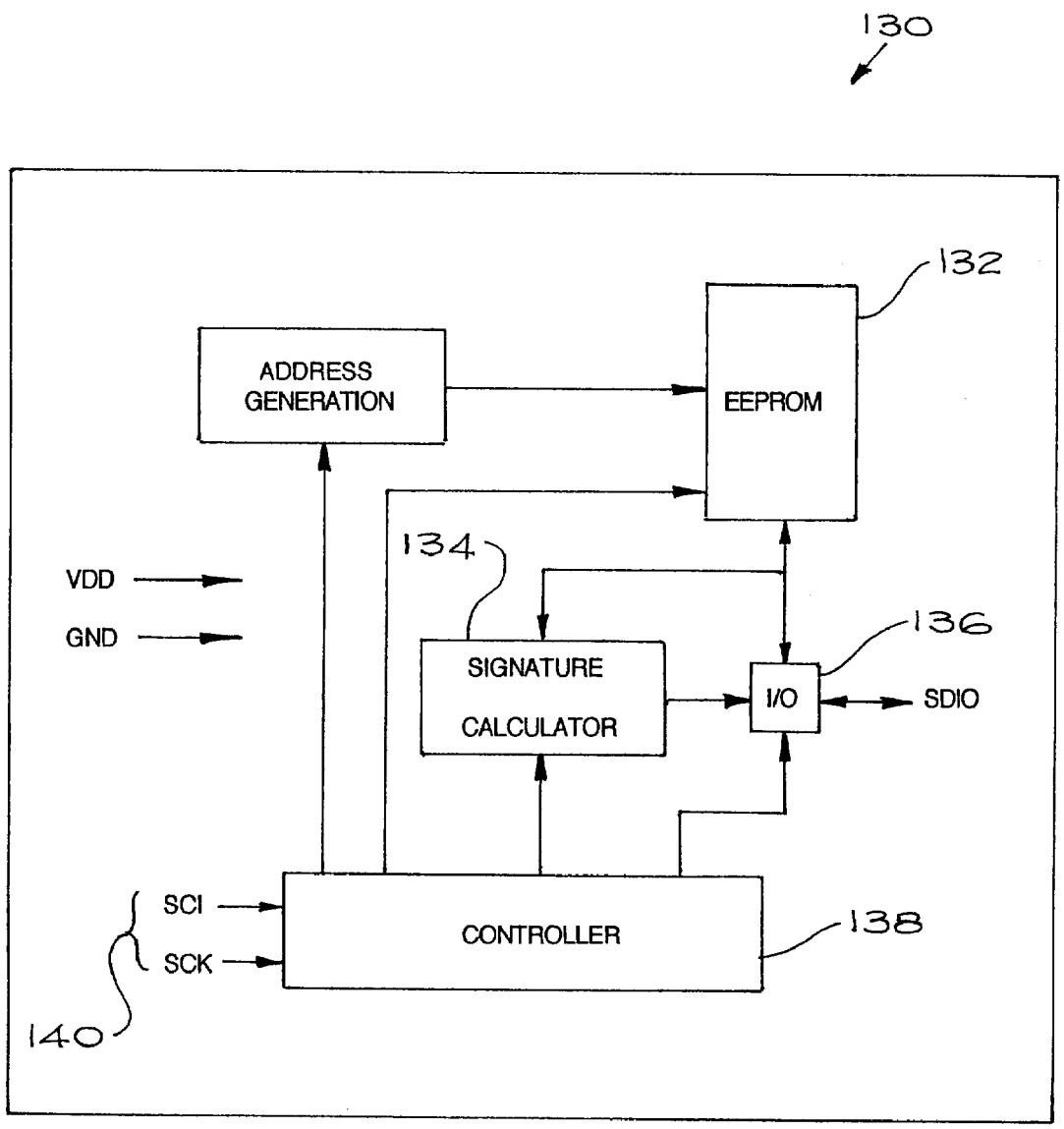
FIG. 6 is a block diagram of one preferred component of the medical probe shown in FIG. 1.

As noted above, in one highly preferred embodiment of the invention, a token card chip is used as the memory storage component 26. One suitable device is the Keeloq™ Token Card Chip SCS152 manufactured by Microchip Technology Inc. The Data Sheets related to the SCS152 published by Microchip Technology Inc. in 1997 are hereby incorporated by reference. Referring now to FIG. 6, a block diagram reproduced from the referenced data sheet is shown at 130. The token card chip provides memory storage 132 for maintaining a token count value, additional undefined memory storage, a signature calculator 134, a serial input/output port 136, a controller 138, and a command interface 140 comprising two inputs. The signature calculator comprises a built-in security function, thereby eliminating the need to provide additional encryption software. A count value is initialized in the device to provide a use value for the present applications. The token card chip described requires an external signal to change the count value, however, similar devices that automatically change the count value are also available. The command interface 140 and serial input/output port 136 can be coupled to external controllers such as the controller 16 described previously, serial interface devices and other known components to provide memory storage and use value information as described above.

One advantage of the token count chip is that the chip has very low power requirements, and can be powered directly from the power lines routed to the light emitting devices in traditional systems. Connecting the chip to these power lines eliminates the need for additional wiring and prevents tampering to remove power to the counting device.

Figure 7:
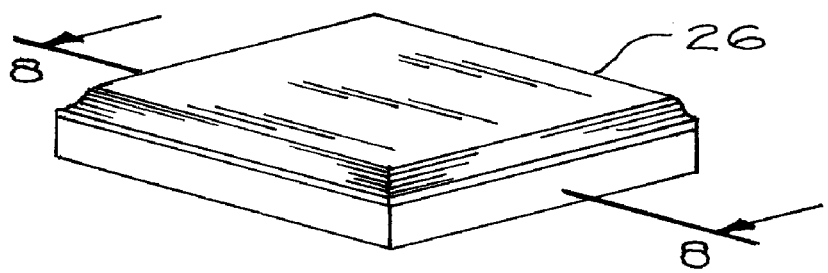
FIG. 7 is a simplified isometric view of one embodiment of a memory storage component of FIG. 1.
Figure 8:
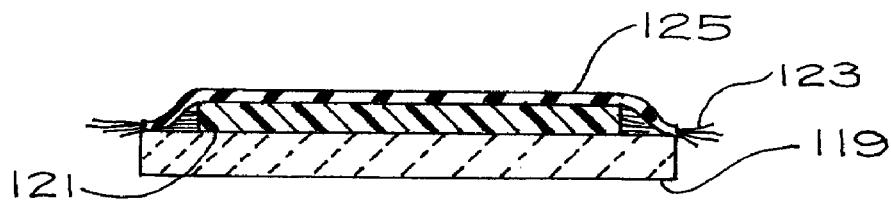
FIG. 8 is a section view along the line 8—8 shown in FIG. 7.

The token card chip, and other available devices suitable for the present application, are preferably small to fit on the back of the connector 122. Preferably, the token card chip is constructed in a configuration commonly known as the "chip on a shingle". (FIGS. 7 and 8) Chips of this type comprise a glass or ceramic layer 119, a semiconductor layer 121, and a plurality of surface mount-type connectors 123 extending from the side of the semiconductor layer. The chip is consequently very small and can be easily slid onto a connector and soldered in place, thereby minimizing the size of the medical probe 14. Once the chip is soldered to the connector 120, a coating layer 125 is preferably layered over the chip to protect the chip and prevent inadvertent contact with adjacent connecting elements. This layer may comprise liquid tape or any of a number of commonly known substances.

When the medical probe 14 is constructed to include the token card chip, the monitoring device 12 includes the appropriate hardware and software to interface to the token card chip. Operation of this system is described more fully in U.S. Pat. No. 5,841,866, which is incorporated herein by reference. Generally, however, interfacing equipment must include the ability to complete the security function including the keys required to encrypt and decrypt secure communications and the ability to decrement the token count value.

In another highly preferred embodiment, the memory storage component 26 comprises an EEPROM produced by Dallas Semiconductor, part number DS2430A. The data sheet for this component, as published by Dallas Semiconductor, is hereby incorporated by reference.

The EEPROM is a small, low-powered chip including only three leads: power, ground, and a serial communications pin. A unique serial number is burned into each device during a manufacturing stage, thereby allowing easy identification. The memory further includes a CRC to verify the data contents. The device, therefore, provides many security advantages.

Like the token card chip described above, this device can be coupled directly to the connector 20 to minimize the size and complexity of connections to the medical probe 14. Communications between the memory storage component 26 and the monitoring device 12 are transmitted through the single communication pin, allowing for simple connections and reduced wiring.

While preferred embodiments have been illustrated and described, it should be understood that changes and modifications can be made thereto without departing from the invention in its broadest aspects. Various features of the invention are defined in the following claims.

We claim:

1. A method for limiting the use of a medical probe to a threshold use value, the method comprising the following steps:
   coupling a memory storage component to a medical probe;
   coupling the medical probe to a medical monitoring device;
   coupling the medical probe to a patient;
   retrieving a use value associated with use of the medical probe from the memory storage component;
   decrypting stored data to verify that the use value has not been corrupted or tampered with;
   updating the use value of the medical probe during use; and
   disabling monitoring functions when the use parameter is substantially equivalent to the threshold use value.

2. The method as defined in claim 1, wherein the decrypted stored data is a serial number identifying the fetal sensor device.

3. The method as defined in claim 1, wherein the decrypted stored data is the use value.

4. A method for limiting the use of a medical probe to a threshold use value, the method comprising the following steps:
   coupling a memory storage component to a medical probe;
   coupling the medical probe to a medical monitoring device;
   coupling the medical probe to a patient;
   monitoring a use value of the medical probe;
   disabling monitoring functions when the use parameter is substantially equivalent to the threshold use value;
   storing identifying information in the memory storage of the medical probe; and
   encrypting the identifying information stored in the medical probe, transmitting the encrypted serial number to the monitoring device, and decrypting the serial number in the monitoring device.

5. The method as defined in claim 4, further comprising the step of displaying a message indicating that a new medical probe is required.

6. The method as defined in claim 4, further comprising the step of storing identifying information in a memory storage of the medical monitoring device.

7. The method as defined in claim 6, further comprising the steps of using the stored identifying information to verify the identity of the medical monitoring device.

8. The method as defined in claim 4, further comprising the step of storing a time and date stamp in the medical probe.

9. The method as defined in claim 4, further comprising the step of storing a time and date stamp and the identifying information in the monitoring device.

10. The method as defined in claim 4, further comprising the steps of transmitting a query signal from the monitoring device to the medical probe and waiting for an acknowledge signal from the medical probe device prior to beginning a medical monitoring process.

11. The method as defined in claim 4, wherein the threshold use value comprises a duration of use of the probe in conjunction with a medical device.

12. The method as defined in claim 4, wherein the threshold value is a count of number of uses of the probe in conjunction with a medical device.

13. The method as defined in claim 4, wherein a public key encryption system is used to encrypt and decrypt the transmitting serial number.

14. A limited use fetal sensor device comprising:
   a housing;
   at least one sensor device; and
   a token chip card including a communications port, the token chip card storing a use value for limiting the use of the probe to a predetermined threshold value.

15. A medical monitoring system comprising:
   a medical probe including at least one sensor, a memory storage component, a communications port, a sensor, and a probe connector, wherein the memory storage component includes a use value for limiting a usage of the medical probe, a serial number identifying the medical probe and at least one encryption key; and
   a monitoring device including a monitor connector, a controller, a memory storage device storing a serial number identifying the monitoring device and at least one encryption key, and a communications port, wherein the monitoring device limits the usage of the medical probe to a predetermined threshold value.

16. The medical monitoring system as defined in claim 15, wherein the medical probe is a fetal sensor.

17. The medical monitoring system as defined in claim 15 further comprising a display coupled to the monitoring device.

18. The medical monitoring system as defined in claim 17, wherein the display provides alphanumeric messages relating to the use value or the use threshold.

19. A method for verifying the identity of components of a medical monitoring system to prevent tampering with stored data:
   storing a serial number, an encryption key, and at least one medical monitoring parameter in a memory storage component of a medical probe;

storing a serial number and an encryption key in a memory storage component of a medical monitoring device;

coupling the medical probe to the medical monitoring device, encrypting the serial number stored in the medical probe, transmitting the encrypted serial number to the medical monitoring device, and decrypting the serial number in the medical monitoring device;

verifying the identity of the medical monitoring device through the decrypted data;

allowing the medical monitoring device to access the medical monitoring parameter if the identity of the medical monitoring device is verified; and preventing the medical monitoring device from accessing the medical monitoring parameter if the identity of the monitoring device is not verified.

20. The method as defined in claim 19, wherein the medical monitoring parameter is a use value.

21. The method as defined in claim 19, further comprising the step of storing the medical monitoring parameter in a non-erasable memory component to prevent erasure.

22. The method as defined in claim 21, wherein the memory component is an EPROM.

23. The method as defined in claim 19, wherein the medical monitoring parameters include a use value and a threshold value.

24. A method for maintaining a history of the use of a medical probe, the method comprising the following steps:

storing a serial number identifying the medical probe in a memory component of the medical probe;

storing a date and time stamp in the memory component of the medical probe;

storing the identity of a medical worker associated with a procedure and storing the identity of the medical worker in the memory component of the medical probe;

storing patient data in the medical probe; and retrieving the stored information to provide a history of a medical procedure.

25. The method as defined in claim 24, further comprising the steps of coupling the medical probe to a medical monitoring device, storing the serial number of the medical monitoring device in a memory component of the medical probe, and storing a serial number identifying the medical probe in the medical monitoring device.

26. The method as defined in claim 25, further comprising the step of storing the date and time stamp in the medical probe.

27. The method as defined in claim 25, further comprising the step of storing the identity of the medical worker in the medical probe.

28. The method as defined in claim 25, further comprising the step of storing the patient data in the medical probe.

29. The method as defined in claim 25, further comprising the steps of coupling a medical probe to the medical monitoring device, transmitting a serial number identifying the medical probe to the medical monitoring device, storing the serial number identifying the medical monitoring device in the medical probe, storing the patient data, medical worker identity, and patient data in the medical probe as a cross check of the data in the medical monitoring device.

30. The method as defined in claim 25, further comprising the step of encrypting at least one of the serial number of the medical monitoring device and the serial number of the medical probe to prevent tampering.

31. A limited use fetal sensor device comprising:

a housing;

at least one sensor device; and a memory storage component storing a protected use value for limiting the use of the probe to a predetermined threshold value, wherein the memory storage component further includes a medical history of the use of the fetal sensor device.

32. The fetal sensor device as defined in claim 31, wherein the memory storage component includes an encrypted serial number identifying the fetal sensor device.

33. The fetal sensor device as defined in claim 31, wherein the memory storage component further includes an encrypted serial number of each of a plurality of medical devices to which the fetal sensor device has been connected.

34. A medical monitoring system comprising:

a medical probe including at least one sensor, a token card chip, a communications port, a sensor, and a probe connector, wherein the token card chip includes a use value for limiting a usage of the medical probe and a serial number identifying the medical probe; and a monitoring device including a monitor connector, a controller, a memory storage device storing a serial number identifying the monitoring device, and a communications port, wherein the monitoring device limits the usage of the medical probe to a predetermined threshold value.

* * * * *

UNITED STATES PATENT AND TRADEMARK OFFICE
CERTIFICATE OF CORRECTION

PATENT NO.    : 6,308,089 B1  
DATED         : October 23, 2001  
INVENTOR(S)   : Gerhard von der Ruhr, Dennis E. Bahr and Michael T. Larsen It is certified that error appears in the above-identified patent and that said Letters Patent is hereby corrected as shown below:

<u>Title page,</u>
Item [73], "O.B. Scientific, Inc." should be -- OB Scientific, Inc."

Signed and Sealed this

Fifteenth Day of October, 2002

*Attest:*

JAMES E. ROGAN
*Attesting Officer*       *Director of the United States Patent and Trademark Office*